United States Patent
Watanabe et al.

(10) Patent No.: US 6,413,680 B1
(45) Date of Patent: Jul. 2, 2002

(54) OPTICAL RECORDING METHOD, OPTICAL RECORDING MEDIUM, AND OPTICAL RECORDING SYSTEM

(75) Inventors: Osamu Watanabe; Masaaki Tsuchimori, both of Aichi; Yoshimasa Kawata, Shizuoka; Chikara Egami, Shizuoka; Okihiro Sugihara, Shizuoka; Naomichi Okamoto, Shizuoka; Osamu Nakamura, Osaka, all of (JP)

(73) Assignee: Kabushiki Kaisha Toyota Chuo Kenkyusho, Aichi-gun (JP)

( * ) Notice: Subject to any disclaimer, the term of this patent is extended or adjusted under 35 U.S.C. 154(b) by 0 days.

(21) Appl. No.: 09/257,196

(22) Filed: Feb. 25, 1999

(30) Foreign Application Priority Data

Feb. 26, 1998 (JP) ............................................. 10-046066
Feb. 26, 1998 (JP) ............................................. 10-046069
Feb. 26, 1998 (JP) ............................................. 10-046073
Sep. 14, 1998 (JP) ............................................. 10-260476

(51) Int. Cl.⁷ .............................. G11B 7/24; G01J 1/00
(52) U.S. Cl. ........................ 430/5; 430/290; 430/270.1; 430/22; 430/945
(58) Field of Search ............................... 430/22, 270.1, 430/5, 290

(56) References Cited

U.S. PATENT DOCUMENTS

| | | | | |
|---|---|---|---|---|
| 4,954,380 A | * | 9/1990 | Kanome et al. ............. | 430/945 |
| 4,975,358 A | * | 12/1990 | Sonnenschein et al. ...... | 430/945 |
| 4,980,262 A | * | 12/1990 | Thomas et al. .............. | 430/321 |
| 5,773,174 A | * | 6/1998 | Koizumi et al. ............... | 430/30 |
| 5,894,349 A | * | 4/1999 | Harris et al. .................. | 356/372 |
| 5,928,815 A | * | 7/1999 | Martin ........................... | 430/5 |
| 6,030,743 A | * | 2/2000 | Okamura et al. ............. | 430/203 |
| 6,171,730 B1 | * | 1/2001 | Kuroda et al. ................. | 430/5 |

OTHER PUBLICATIONS

Yanagi et al. "novel and sensitive activity . . . " Enzyme, vol. 28(4) pp 400–403 (1982).*
Polson et al. "Precipitation Analysis . . . ", Methods Immunol. Immunchem. vol. 3, pp 186–188 (1971).*
Susor et al., "Methods for the detection of pyruvate kinase . . . " Analyt. Biochem., vol. 43, pp. 147–155. (1971).*
Fischer et al. "Submicroscopic pattern replication . . . " J. Vac Sci. Technol., vol. 19(4) pp. 881–885 (Dec. 1981).*
Tanaka et al., "Pritning sub–100 nm features . . . ", Jap. J. Appl. Phys. vol. 37(12b) pp. 6739–6744 (1998).*
Abstract of Yanagi et al., "Novel and Sensitive activity . . . " Enzyme, vol. 28(4) pp. 400–403 (1982).*
Abstract of Polson, et al., "Precipitation analysis . . . " Methods Immunol. Immunchem., vol. 3 pp. 186–188 (1971).*
Stéphane Davy, et al. "Near Field Optics: Snapshot of the Field Emitted By A Nanosource Using a Photosensitive Polymer", Appl. Phys. Lett., vol. 69, No. 22, 1996, pp. 3306–3308.
Almeria Natansohn, et al. "Azobenzene–Containing Polymers: Digital and Holographic Storage", American Chemical Society, 1997, pp. 236–250.

* cited by examiner

Primary Examiner—Martin Angebranndt
(74) Attorney, Agent, or Firm—Oblon, Spivak, McClelland, Maier & Neustadt, P.C.

(57) ABSTRACT

An optical recording method suited for recording a very small object or movement of a living organism such as a microorganism, which comprises irradiating an informative object set on or above a recording layer comprising a photosensitive material capable of undergoing a storable and detectable photochemical reaction, preferably a polymer material containing a photoreactive component capable of photoisomerization and having in the repeating unit thereof at least one group selected from a urethane group, a urea group, an amide group, a carboxyl group and a hydroxyl group, and recording a distribution of an optical near field generated from the informative object being irradiated on the photosensitive material as a photoreacting quantity of the photosensitive material.

23 Claims, 7 Drawing Sheets

OPTICAL RECORDING METHOD, OPTICAL RECORDING MEDIUM, AND OPTICAL RECORDING SYSTEM

BACKGROUND OF THE INVENTION

1. Field of the Invention

This invention relates to an optical recording method, an optical recording medium, an optical recording system, and a method for observing a sample. More particularly, it relates to an optical recording method and an optical recording system making use of a distribution of an optical near field produced from an informative object being irradiated, an optical recording medium having excellent heat resistance, and application of the optical recording method to sample observation.

2. Description of the Related Art

Methods for optically recording information on a recording medium comprising irradiating the recording medium with, for example, a condensed recording light beam from a laser light source to change the reflectance, etc. of the recording medium and recording the change are known. However, not only a laser beam but any other optical systems utilizing light transmitted through gas, etc. cannot be made use of in the region below the diffraction limit of the light. Recording densities smaller than the scale of the diffraction limit can never be achieved, nor can be recorded information of an object smaller than the diffraction limit.

In recent years a so-called optical near field has been attracting attention in this connection. An optical near field can be localized in regions smaller than the wavelength of the light on the surface of an object. Hence, application of an optical near field to high-density recording systems and high-resolution optical microscopes has been proposed.

For example, Motoichi Ohtsu made a report on an optical near field microscope called "C mode" or "I mode" in his paper titled "The Present and Future Development of Optical Near Field Microscope" (*Kikai no kenkyu,* Vol. 49, No. 5 (1997)). The optical near field microscope of C mode picks up evanescent light (optical near field) generated on the surface of a sample being irradiated, by scanning with a fine probe to provide optical data, which are processed to give a three-dimensional image of the surface of the sample. The optical near field microscope of I mode uses a fine probe through which light is transmitted to ooze out an optical near field oozes from its tip. The surface of a sample is scanned with this fine probe to convert the optical near field to scattered light thereby furnishing information data of the sample surface.

However, the above-described optical near field microscopes of C mode and I mode involve the following disadvantages.

(1) Because the probe is brought close to a sample to be observed, it greatly disturbs the electric field around the sample. Therefore, the resulting image is difficult to interpret.

(2) Because a scatter type probe having a very small opening or a very small diameter at the tip is used, the detectable light intensity is small, and the signal/noise ratio (S/N ratio) is not sufficient.

(3) Such processing as integration is necessary for improving the S/N ratio. Considering that scanning with the probe needs some time, the microscope meets difficulty in making an observation on high-speed phenomena or biological cells.

As to optical recording media used in various optical recording methods, it has been keenly demanded to develop a recording medium having high record durability (especially heat resistance) and/or having recorded practically advantageous information.

S. Davy and M. Spajer report in their paper "Near Field Optics: Snapshot of the field emitted by a nanosource using a photosensitive polymer" (*Appl. Phys. Lett.,* Vol. 69, No. 22, p. 3306 (1996)) a technique comprising applying an optical near field generated from the tip of a probe to a photosensitive polymer film of an acrylic polymer having an azo dye in the side chain thereof to produce unevenness, which is not optical information recording. This technique is to record the optical near field of a light source. A method for recording the optical near field of an informative object is not disclosed in their report. Nor is given consideration to the thermal stability of the record.

JP-A-61-287791 discloses an optical recording medium making use of a condensational polymer dye, which is characterized by inertness to photo-induced chemical degradation or change of optical properties.

SUMMARY OF THE INVENTION

A first object of the present invention is to provide an optical recording method, an optical recording system, an optical recording medium, and a method for observing a sample which are free from the above-described disadvantages (1) to (3) and to provide a technique of optical near field memory for achieving an ultrahigh recording density of several tens of gigabites per square inch and a photolithographic technique applicable to the region below the light diffraction limit.

A second object of the present invention is to provide an optical recording medium having excellent record durability, particularly heat resistance.

The inventors of the present invention have found that, when an informative object (a sample for observation or an object for putting information in) is positioned on or above the surface of a photosensitive material, and that area of the photosensitive material is irradiated with light, photochemical reaction of the photosensitive material takes place more strongly with the optical near field at the part where the irradiated informative object is positioned than with the irradiating light at other irradiated parts. The first object of the invention is accomplished based on this finding.

The inventors have also found that the second object of the invention is accomplished by an optical recording medium prepared by using a polymer containing a photoreactive component capable of photoisomerization and having in the repeating unit thereof at least one group selected from a urethane group, a urea group, an amide group, a carboxyl group and a hydroxyl group. Based on this finding, there are provided a recording medium capable of recording optical information furnished from light for irradiation or an optical near field in a variety of modes, a recording medium useful for holography, a recording medium which contains a specific photoreactive component capable of recording, reading out and erasing information and providing a durable and heat-resistant record, and a recording medium having effectively recorded thereon changes of an informative object with time.

The first object of the invention is accomplished by the following 1st to 4th aspects, and the second object of the invention is achieved by the following 5th to 8th aspects.

The 1st aspect of the invention is an optical recording method comprising constituting a recording layer of a photosensitive material capable of undergoing a storable and detectable photochemical reaction, setting an informative object on or above the recording layer at such a position that an optical near field generated from the informative object may reach the recording layer, irradiating at least the area of the recording layer where the informative object is positioned with light to cause the informative object to generate the optical near field, and recording the distribution of the optical near field on the photosensitive material as a photoreacting quantity of the photosensitive material.

The 2nd aspect is an optical recording method comprising constituting a recording layer of a photosensitive material capable of undergoing a storable and detectable photochemical reaction, setting a mobile or moving informative object on or above the recording layer, irradiating at least the area of the recording layer where the informative object is positioned with light to cause the informative object to generate the optical near field, and recording the distribution of the optical near field on the photosensitive material as a photoreacting quantity of the photosensitive material, the irradiation and recording being repeated two or more times in accordance with the movement of the informative object.

The 3rd aspect provides an optical recording system comprising a recording layer on or above which an informative object is positioned and which is constituted by a photosensitive material capable of undergoing a storable and detectable photochemical reaction, and a light source capable of irradiating at a time at least the area of the recording layer where the informative object is positioned.

The 4th aspect provides a method for observing a sample comprising a recording process comprising constituting a recording layer with a photosensitive material capable of undergoing a storable and detectable photochemical reaction, setting a sample to be observed on or above the recording layer at such a position that the optical near field generated from the sample being irradiated may reach the recording layer, irradiating at least the area of the recording layer where the sample is positioned to cause the sample to generate an optical-near field, and recording the distribution of the optical near field on the photosensitive material as information corresponding to the photoreacting quantity of the photosensitive material, and an observing process comprising observing the recorded information by an observing means selected according to the recording mode.

The 5th aspect resides in an optical recording medium comprising a recording layer for recording optical information with light for irradiation or a generated optical near field, wherein the recording layer comprises a polymer material containing a photoreactive component capable of photoisomerization and having in the repeating unit thereof at least one group selected from the group consisting of a urethane group, a urea group, an amide group, a carboxyl group and a hydroxyl group.

The 6th aspect is an optical recording medium for holography, which has a recording layer comprising a polymer material containing a photoreactive component capable of photoisomerization and having in the repeating unit thereof at least one group selected from the group consisting of a urethane group, a urea group, an amide group, a carboxyl group and a hydroxyl group.

The 7th aspect furnishes an optical recording medium capable of recording, reading out and erasing information which has a recording layer comprising a polymer material containing a photoreactive component which is capable of photoisomerization and the molecular orientation of which can be controlled by light and having in the repeating unit thereof at least one group selected from the group consisting of a urethane group, a urea group, an amide group, a carboxyl group and a hydroxyl group.

The 8th aspect affords an optical recording medium having a recording layer comprising a photosensitive material capable of undergoing a storable and detectable photochemical reaction, the recording layer having recorded thereon at least one of the following pieces of information (1) to (4) in such a mode that a distribution of an optical near field generated from an informative object being irradiated is recorded:

(1) a record of an instantaneous form of a moving informative object;
(2) a record of movement of an informative object which is a fine particle movable by radiant pressure of light;
(3) a record of movement of an informative object which is an autonomically moving living organism; and
(4) a record of changing history of an informative object which shows change with time that can be recorded as optical information.

DETAILED DESCRIPTION OF THE INVENTION

[Optical Recording]

Figure 1:
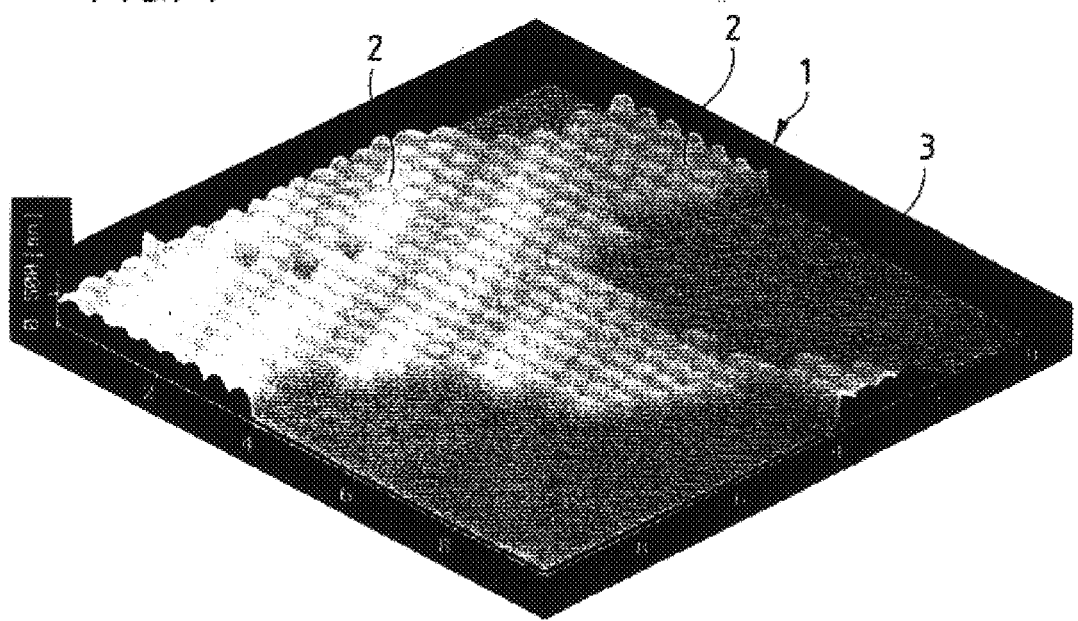
FIGS. 1 through 6 are micrographs obtained under an atomic force microscope in Examples.

The term "optical recording" as used herein has a broader sense than the term "information recording" as commonly intended. That is, it not only means recording for storing the information from an informative object having known information converted but includes the case in which an informative object is per se an object of analysis as in optical near field microscopic analysis, and its analytical data are recorded. The term is also applied to the case in which an informative object is used as information and a means for fine photoprocessing of a photosensitive material as in semiconductor lithography.

The 1st to 3rd aspects of the invention will be described in detail.

[Photosensitive Material]

Any photosensitive material capable of undergoing an arbitrary storable and detectable photochemical reaction can be used in the invention with no particular limitation. For example, materials which undergo photoisomerization, etc. in accordance with light intensity to produce unevenness on its surface in agreement with the reaction quantity. Polymer materials are particularly preferred. Photoisomerization is a preferred photochemical reaction for its rapidness in response to light.

Where unevenness is formed on the surface of the photosensitive material, there is an advantage that information of an informative object is recorded as a physically fixed shape that can be observed with a means having overwhelmingly higher spacial resolution than optical microscopes, such as an atomic force microscope (AFM), a scanning tunnelling microscope (STM), a scanning electron microscope (SEM), and the like.

Photosensitive materials showing changes in refractive index or absorbance in accordance with light intensity are also useful. In this case, too, the information recorded as a refractive index or absorbance distribution can be observed or detected by an appropriate known means such as an optical near field microscope.

While polymeric photosensitive materials are generally preferred, other photosensitive materials are also employable. Of polymer materials, condensational polymer materials such as polyester, polyamide, polyurethane, and polyurea are particularly preferred for their high capacity of introducing photoreactive sites for photoisomerization, etc.

[Recording Layer]

The recording layer is not particularly limited in shape as long as a sample to be observed can be positioned on or above it, while a flat surface made of a film of the photosensitive material is generally convenient for optical recording and for observation and/or detection of the recorded information. In carrying out optical recording for photoprocessing, an arbitrary surface of the object of photoprocessing serves as a recording layer. The recording layer can have an arbitrary area according to necessity.

The recording layer is usually placed in the atmosphere but, if desired, under pressure or reduced pressure. In observing microorganisms, etc., the recording layer can be covered with a water droplet or, in some cases, the essential part or the whole of the system may be immersed in liquid, e.g., water.

[Informative Object]

The term "informative object" as intended in the invention includes various embodiments, such as an object having converted known information to be optically recorded, an object to be analyzed, a processing means for carry out fine photoprocessing, and the like.

The informative object is not essentially limited in shape, size or material as long as it generates an optical near field on being irradiated. When used for optical information recording or photoprocessing, the informative object preferably has a controlled shape, controlled transparency or a controlled refractive index from the standpoint of accuracy. Where only one side of an informative object (for example, the side opposite to the recording layer) is irradiated, it is preferred for the informative object to have light transmitting properties above a certain level or to have a small size enough to generate an optical near field on its side in contact with or facing to the recording layer.

The size of the informative object may be either above or below the diffraction limit of irradiating light. Where it is used for high density optical information recording, it is desirable that a single recording bit be formed within a range equal to or smaller than the diffraction limit. More specifically, the informative object is preferably 100 nm or smaller in size to realize a recording density as high as several tens of gigabites per square inch (Gbit/in$^2$) or even higher. A still preferred size is 25 nm or smaller for achieving a recording density of 1 Tbit/in$^2$. While not limiting, the material of the informative object preferably includes transparent glass and polymers for controllability and handling properties.

The informative object to be irradiated is preferably set at a position within a several hundreds of nanometers' distance from the recording layer so that an optical near field generated from the informative object being irradiated may reach the recording surface. A still preferred distance from the recording layer is within 100 nm so that a sufficient optical near field generated from the informative object may reach the recording layer to realize accurate recording. It is particularly preferred for the informative object to be positioned in direct contact with the recording layer when irradiated. In this case, the optical near field sufficiently and certainly reaches the recording layer to further enhance the accuracy of recording.

[Irradiating Light]

The wavelength of irradiating light is not particularly limited and can be selected appropriately in conformity with the photosensitive material making up of the recording layer. Seeing that an optical near field generated from an irradiated informative object is absorbed by the photosensitive material to cause a prescribed photochemical reaction, wavelengths showing a high absorption efficiency are preferably selected. In general, rays from the ultraviolet to near infrared region are chosen.

The light source for irradiation is not particularly limited and can be selected appropriately according to the optical near field to be recorded. In view of reproducibility in forming unevenness as a recording mode or ease in the analysis following, a laser light source is preferred.

The intensity of light or time of irradiation is not limited and is selected appropriately in accordance with the photoreactivity, and the like of the photosensitive material. In recording high-speed movement of an informative object by repeating short time exposure, pulse light having a high peak power can be used.

With respect to the range to be irradiated, the language "the area where an informative object is positioned" as used herein denotes the range of the surface area of the recording layer containing the informative object. A requisite or useful area range is decided arbitrarily in accordance with the purpose of the optical recording.

[Distribution of Optical Near Field]

The language "distribution of an optical near field generated from an informative object being irradiated" used as for the 1st aspect of the invention chiefly means pieces of information relating to the shape and position of an informative object. The same language used as to the 2nd aspect of the invention additionally means pieces of information relating to a trace or form of movement of an informative object or change of an informative object in characteristics with time.

The 1st aspect of the invention produces the following actions and effects.

When the area of the recording layer containing an informative object is irradiated, the photochemical reaction induced by the action of the optical near field in the area where the informative object is positioned is stronger than the photochemical reaction induced by the irradiating light on the other area. As a result, the distribution of the optical near field generated from the informative object is reflected as a difference in photochemically reaction quantity of the photosensitive material between the irradiated area and non-irradiated area. The mechanism of such a phenomenon could be attributed to various causes and has not been proved definitely as yet. For example, the higher refractive index of an informative object than that of the light transmitting medium (e.g., air) may have some influences, or an optical near field may have such properties that induce a particularly strong photochemical reaction.

According to the present invention, there is no need to use a probe for picking up only the optical near field of an informative object as in the above-mentioned conventional C mode nor a probe for causing an optical near field to act only on an informative object as in the conventional I mode. Therefore, recording completes simply by irradiating once without requiring the time for scanning with a probe. The above-described other disadvantages accompanying the use of a probe are also eliminated.

Since optical recording completes through a single irradiating operation, there is no such a recording failure that may occur where an informative object is a very small substance or a living organism (especially a microorganism) which moves or varies its refractive index distribution with time. Because the whole of the predetermined area is irradiated at a time, it is possible to simultaneously record a variety of informative objects positioned randomly in that area, to simultaneously record a number of informative objects that are positioned with some informative intention, or to record all pieces of information of a large informative object at a time.

The optical record obtained by the present invention can be subjected to observation and/or detection by making use of an arbitrary and advantageous means for observing and/or detecting in conformity with the photochemical reaction type either immediately after recording or anytime after storage.

Taking advantage of an optical near field, the optical recording method of the invention can be applied to high-density optical information recording, high resolution optical analysis or fine photoprocessing in a region equal to or smaller than the light diffraction limit.

The 2nd aspect of the invention produces the following actions and effects in addition to those described as to the 1st aspect.

The movability of an informative object, such as a fine particle movable by radiation pressure of light or an autonomically moving microorganism, rather enhances the merit of the 2nd aspect. That is, irradiation being repeated to cope with the movement of such an informative object, not only the static information, such as the shape, but the movement or change in shape or properties of the informative object can be recorded.

For example, the method is effective in optically recording a phenomenon that a very small informative object is aligned along the electric field distribution on receiving the radiation pressure of light. This phenomenon can be made use of in optically recording the trace of movement of the informative object while controlling the movement, or in performing photoprocessing at the moving site. Where an informative object is accompanied by change in properties or form, the method can be used to obtain an image showing the change with time. Further, the moving state or cell division or conjugation of a microorganism can be traced.

In carrying out the above-described recording, short pulse light can be used to record a high-speed phenomenon continuously so that the phenomenon may be observed later slowly.

The 3rd aspect of the present invention has the following actions and effects.

The optical recording system of the 3rd aspect makes it feasible to effectively carry out the optical recording according to the 1st and/or 2nd aspects. Requiring neither a probe nor a probe-related drive/control/optical system, the optical recording system enjoys considerable simplification and reduction in cost.

The 4th aspect of the invention will be described in detail.
[Photosensitive Material]

Any photosensitive material capable of undergoing an arbitrary storable and detectable photochemical reaction can be used with no particular limitation. For example, photoreactive polymers are used for formation of unevenness on the recording layer. Photoconductive materials are used for developing an electric potential difference on the recording layer. Photorefractive materials are used for making a change in refractive index.

Photoreactive polymer materials are polymers having a photoreactive site for absorbing light and thereby undergoing a reaction. Polymers capable of photoisomerization, etc. depending on the light intensity to product unevenness on its surface in accordance with the reaction quantity are preferred. Photoisomerization is a preferred photochemical reaction for its rapidness in response to light. These polymer materials are also effective in producing recordable changes of optical characteristics, such as a refractive index and an absorbance. Condensational polymers, such as polyester, polyamide, polyurea, and polyurethane, are preferably used for their high capacity of introducing photoreactive sites.

The photoconductive materials, which maybe either organic or inorganic, preferably include bismuth silicon oxide, and a polymer blend or copolymer comprising an electroconductive polymer.

The photorefractive materials, which may be either organic or inorganic, preferably include lithium niobate and a polymer blend or copolymer comprising an electroconductive material and a nonlinear optical material.
[Recording Layer]

The recording layer is not particularly limited in shape as long as a sample to be observed can be positioned on or above it, while a flat surface made of a film of the photosensitive material is generally convenient for the recording process and the following observing process.

The recording layer is usually placed in the atmosphere in the recording process but, if desired, under pressure or reduced pressure. In observing microorganisms, etc., the recording layer can be covered with a water droplet or, in some cases, the essential part or the whole of the system may be immersed in liquid, e.g., water, or a specific gas.
[Sample to Be Observed]

The sample to be observed is usually a very small object or a microorganism but is not essentially limited in shape, size or material as long as it generates an optical near field on being irradiated. Where only one side of a sample (for example, the side opposite to the recording layer) is irradiated, it is preferred for the sample to have light transmitting properties above a certain level or to have a small size enough to generate an optical near field on its side in contact with or facing to the recording layer.

The size of the sample may be either above or below the diffraction limit of light for irradiation. The advantages of the 4th aspect of the invention are manifested particularly effectively when applied to samples having a size equal to or smaller than the diffraction limit.
[Irradiating Light]

The wavelength of light used for irradiation is not particularly limited and can be selected appropriately in conformity with the photosensitive material making up the recording layer and a sample to be observed. Seeing that an optical near field generated from a sample being irradiated is absorbed by the photosensitive material to cause a prescribed photochemical reaction, wavelengths showing a high absorption efficiency are preferably selected. In general, rays from the ultraviolet to near infrared region are chosen.

The light source for irradiation is not particularly limited and can be selected appropriately according to the optical near field to be recorded. In view of reproducibility in unevenness formation as one of recording modes or ease in the following analysis, a laser light source is preferred.

The intensity of light and the time of irradiation are not limited, either. They are decided appropriately in accordance with the photoreactivity, and the like of the photosensitive material. In recording high-speed movement of a sample by repeating short time exposure, pulse light having a high peak power can be used.

[Recording of Moving Sample]

The observing method of the 4th aspect is applicable to observation of a moving sample or a sample being moved. It is known that, when light rays illuminate a very small sample of, for example, several nanometers to several tens of nanometers to show reflection or refraction, the momentum of photons changes to exert force on the sample. It follows that the sample under observation is pushed or pulled by the radiation pressure of light. Accordingly, it is possible to make a small sample, e.g., microbial cells, move by controlling the light intensity thereby to observe the sample on another predetermined site of the recording layer. This is effectively applicable to an embodiment in which a sample whose shape or recordable properties change with time is successively recorded with time while being made to move by irradiation with pulse light, an embodiment in which two samples are made to move to the same site of observation where they undergo reaction with each other, and the reaction result is recorded, or an embodiment in which movement, cell division or cell conjugation of a microorganism is traced.

The wavelength of the light for controlling the movement of a very small sample and that of the light for furnishing image information may be changed to improve the accuracy of recording and observation.

In continuous recording, every individual image obtained is a record resulting from instantaneous irradiation. Therefore the image obtained is free from blur or recording failure that may be caused by the change of the sample in position or properties.

[Observing Process]

Where the recording process is to form unevenness on the recording layer of the photosensitive material, there is an advantage that information of a sample is recorded as a physically fixed shape that can be observed with a means having overwhelmingly higher spacial resolution than optical microscopes, such as AFM, STM, SEM, Transmission Electron Microscope (TEM), Scanning Frictional Force Microscope, and the like.

The information recorded as a refractive index distribution or an absorbance distribution can be read out and/or observed by means of a scanning near-field optical microscope, and the information recorded as a change in surface electric potential of the recording layer can be read out and/or observed by means of a surface electric potential microscope (e.g., scanning Maxwell stress microscope or a scanning Kelvin probe force microscope), and so forth.

The 4th aspect of the invention produces the following actions and effects.

In the recording process (A), the area of the recording layer containing a sample is irradiated with light whereby a photochemical reaction takes place in the area where the sample is positioned by the action of the optical near field generated by the sample, and this reaction is stronger than the photochemical reaction which takes place in the other irradiated area. As a result, the distribution of the optical near field generated from the sample is recorded on a level different from the level of the surrounding area as information corresponding to the photoreacting quantity of the photosensitive material.

The mechanism of such a phenomenon could be attributed to various causes and has not been proved definitely as yet. For example, the higher refractive index of a sample than that of the light transmitting medium (e.g., air) may have some influences, or an optical near field may have such properties that induce a particularly strong photochemical reaction.

According to the recording process (A), there is no need to use a probe for picking up only the optical near field of a sample as in the above-mentioned conventional C mode nor a probe for causing an optical near field to act only on a sample as in the conventional I mode. Therefore, recording completes simply by irradiating once without requiring the time for scanning with a probe. The above-described other disadvantages accompanying the use of a probe are also eliminated.

Since the recording process (A) takes advantage of an optical near field, it achieves a resolving power corresponding to the light diffraction limit or even finer. Further, exposure with light completes through a single irradiating operation. Therefore, there is no such a recording failure that may occur where a sample is a very small substance or microorganism which moves autonomically or be moved by the radiation pressure of light. It has now been made feasible to make an observation of a sample that is moving at a high speed with a higher resolving power than the light diffraction limit. By repeating short time exposure with pulse light, a moving sample can be observed as a series of still images.

Moreover, a predetermined area of the recording layer is irradiated with light at a time, all the variety of, or a large number of, objects present in that area can be recorded simultaneously.

The optical record obtained by the recording process (A) is observed or read out in the observing process (B) either immediately after recording or anytime after recording. The means for observing or reading out the optical record is selected appropriately according to the type of the photochemical reaction (i.e., the mode of optical recording).

Because the object of observation is fixed on the recording layer of the photosensitive material as optically recorded information, the disadvantage due to unexpected movement of the object is eliminated. Even where the means of observation have many restrictions on use, for example, a scanning tunneling microscope or a scanning atomic force microscope, observation or reading out can be carried out making use of the merits of these means without being hindered by the restrictions.

The 5th aspect of the invention will now be explained in detail.

[Optical Recording Medium]

The optical recording medium of the 5th aspect may comprise, in addition to the recording layer comprising the above-described polymer material, other constituent members, such as a substrate, a protective film, and a reflective film.

The optical recording medium can be used as a medium for recording optical information in various known applications, for example, a recording medium for calculators, an audio-visual recording medium, a recording medium for recording an optical near field intensity distribution.

For example, the optical recording medium can be used as a medium for writing only once like CD-R, on which information is recorded in the form of unevenness, etc. for every bit by use of an optical near field microscope or all at once by irradiation of light through a mask to provide read-only memory (ROM). Information of an object to be observed can be recorded by putting the object on the recording medium, irradiating the object, and recording the intensity distribution of the thus generated optical near field on the recording medium in the form of unevenness, etc.

The information recorded as unevenness can be read with an atomic force microscope, a stylus-type profiler, a laser displacement meter, etc. The information recorded as a refractive index distribution can be read with a phase-contrast microscope, an optical near field microscope, etc. The information recorded as a difference of orientation of the photoreactive component (hereinafter described) can be read from a polarized visible or infrared light absorption spectrum, etc.

[Recording Mode and Structure]

The information recorded on the optical recording medium can have various modes of recording based on the photoisomerization reaction of the photoreactive component. Such recording modes include change or difference occurring on the surface of the optical recording medium (i.e., surface recording layer), such as unevenness, a change in refractive index or refractive index anisotropy, a change in absorbance or absorbance anisotropy, a difference in degree of orientation of the photoreactive component, and theses changes or differences in optical characteristics which occur in a recording layer or layers provided inside the optical recording material.

A change in refractive index or absorbance or a difference in degree of orientation of the photoreactive component can also be induced by using irradiating light transmitted through air, etc. and recorded on the surface of the optical recording medium or the recording layer or layers provided inside the recording medium.

While the light used for recording and detecting information, i.e., writing and reading information is not particularly limited, ultraviolet light, visible light or near infrared light are preferably used in practice.

The optical recording medium of the invention can have a single recording layer or a plurality of recording layers, sometimes 100 or more recording layers. In the former case, information is recorded on the surface of the medium (surface recording layer) or on a single recording layer which is provided inside of the medium for the purpose of protecting the record. Where information is recorded on the surface recording layer, the recorded side or both sides of the medium can be protected by coating with a protective film.

In the latter case, information is recorded on the surface recording layer and one or more recording layers provided inside the medium, or information is recorded on two or more recording layers provided inside the medium. A plurality of thin optical recording medium units arbitrarily selected from those having a single recording layer (i.e., the surface recording layer or the inside recording layer) and those having two or more recording layers can be joined to provide an optical recording medium having a plurality of recording layers.

Where the optical recording medium has two or more recording layers, the recording modes do not need to be the same in all the recording layers. For example, information may be recorded on the surface recording layer as unevenness by making use of an optical near field, on an inside recording layer as a refractive index distribution, and on another inside recording layer as an absorbance distribution. If desired, a buffer layer which does not participate in recording may be provided between adjacent recording layers for the purpose of reducing cross talks between them.

[Polymer Material]

The polymer material which can be used in the optical recording medium of the invention is not limited except that it is a polymer containing a photoreactive component capable of photoisomerization and having in the repeating unit thereof at least one group selected from the group consisting of a urethane group (—O—CO—NH—), a urea group (—NH—C—NH—, —NH—CO—N= or —NH—CO—N<), an amide group (—CO—NH—), a carboxyl group and a hydroxyl group.

The degree of polymerization of the polymer is not particularly limited as far as is consistent with moldability, e.g., film forming properties. The polymer may be either a homopolymer or a copolymer and can have an arbitrary molecular structure, such as a linear structure, a branched structure, a ladder structure, a star-burst structure, etc. The form of the copolymer includes a block copolymer, a random copolymer, a graft copolymer, and so forth. When particularly improved heat resistance is expected, a polymer having a ring structure, e.g., a phenylene group, in its main chain is preferred.

The language "containing a photoreactive component" as used as for the polymer material constituting the optical recording medium of the invention means that a photoreactive component is bonded to the polymer through a chemical bond, such as a covalent bond, an ionic bond or a coordinate bond, as hereinafter described in detail. Such a photoreactive component preferably includes those having at least one of an azo group, a C=C group and a C=N group which are capable of trans-cis photoisomerization.

On being irradiated with light having a usual intensity, the photoreactive component capable of trans-cis photoisomerization changes its trans to cis configurational ratio. Because the trans-form and the cis-form differ in optical characteristics such as refractive index and absorbance, the difference in the configurational ratio between the irradiated area and non-irradiated are a makes recording possible. When irradiated with high intensity light, on the other hand, the double bond of N=N, C=C or C=N is reacted to produce low molecular weight segments. The low molecular weight segments evaporate off to cause a reduction in density or a change in shape (e.g., formation of a depression of the polymer material), which makes recording possible.

Further, a so-called optical poling effect on the photoreactive component capable of trans-cis photoisomerization can be taken advantage of. The photoreactive component capable of trans-cis photoisomerization is generally anisotropic as to light absorption. For example, when a polymer having a trans-4-amino-4'-nitroazobenzene structure as a photoreactive component is irradiated with light of 488 nm that is polarized in the direction parallel to the direction connecting the amino group and the nitro group, the above structure undergoes photoisomerization into a cis-configuration at a higher probability than with polarized light equal in wavelength or intensity but different in direction of polarization. Next, the cis-configuration changes into two kinds of trans-configuration by light or heat. One (A) shows the direction connecting the amino group and the nitro group almost parallel to the direction of polarized incident light, and the other (B) shows the direction connecting the amino group and the nitro group almost perpendicular to the direction of polarized incident light. In this regard, although the probabilities of producing the trans-configurations (A) and (B) are almost the same, that of absorbing the trans-configuration is different depending on anisotropy of absorbance. As a result, the above (A) to (B) ratio of the photoreaction component decreases to change the orientation distribution, and information can thus be recorded by making use of the difference of orientation distribution between the irradiated area and non-irradiated area.

Taking the above observations into consideration, examples of particularly preferred polymers containing a photoreactive component include the polymers used in Examples hereinafter given and, in addition, those having a structure represented by formula (I) to (IV) shown below. In these formulae, —X represents a nitro group, a cyano group, a trifluoromethyl group, an aldehyde group or a carboxyl group; —Y— represents —N=N—, —CH=N— or —CH=CH—; and —R—, —R$^1$—, —R$^2$— and —R$^3$—, which may be the same or different, each represents a phenylene group, an oligomethylene group, a polymethylene group or a cyclohexylene group.

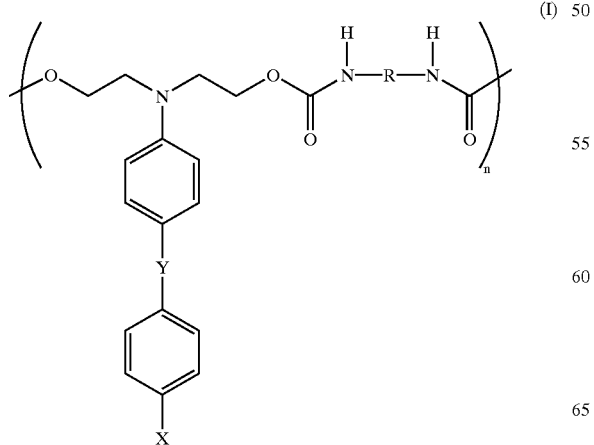

(I)

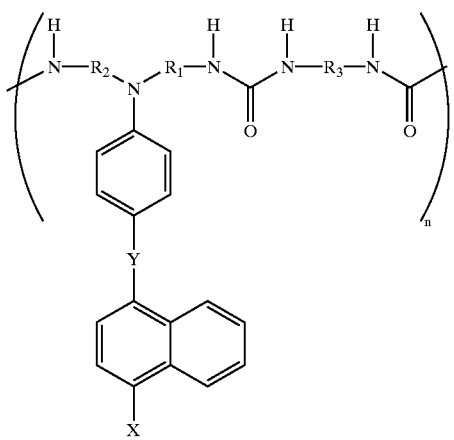

(II)

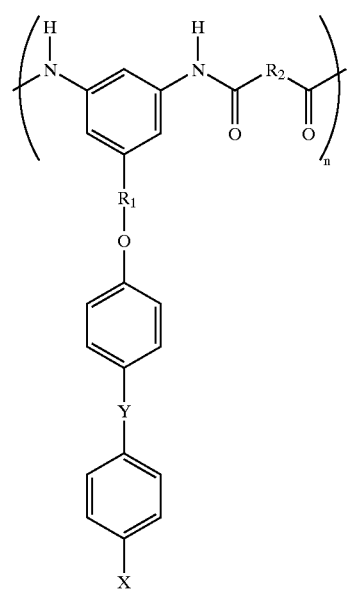

(III)

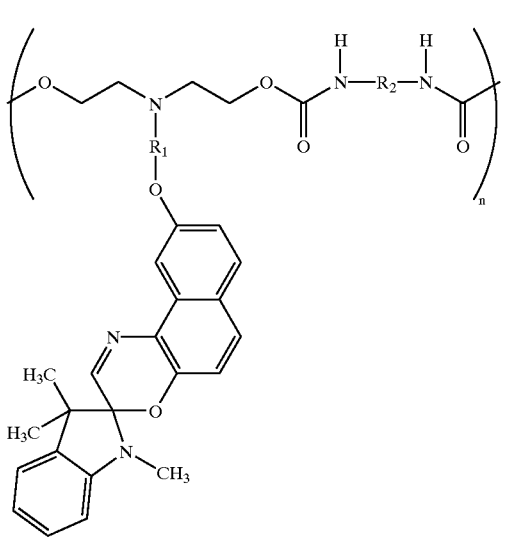

(IV)

Additionally the polymer materials described in Examples or Comparative Examples of the following publications are all employable in the present invention as a polymer material containing a photoreactive component: all the urethane copolymers and polyurethane described in Examples and Comparative Examples of JP-A-8-160477; all the urethane-urea copolymers and polyurethane described in Examples and Comparative Examples of JP-A-8-220575; the polyurethane described in Example 1 and Comparative Example 1 of JP-A-8-87040; the ester-amide copolymers described in Examples 1 and 3 of JP-A-10-90739; and the polyamide described in Examples 3, 4 and 5 of JP-A-9-334794.

It is desirable that larger content of the photoreactive component be present in the polymer material. Chemically bonded to the polymeric structure, the photoreactive component could be present in a high proportion in a uniformly dispersed state in the polymer without suffering from aggregation. A preferred content of the photoreactive component in the polymer is from 30 to 70% by weight. If it exceeds 70% by weight, the monomer(s) tend(s) to fail to achieve a degree of polymerization sufficient for stable formation of a recording layer.

The 5th aspect produces the following actions and effects.

It is known that a urethane group, a urea group, an amide group, a carboxyl group and a hydroxyl group each form a strong hydrogen bond among a kind or different kinds. Existence of at least one of, or at least one kind of, these groups per repeating unit induces intramolecular or intermolecular hydrogen bonding to form a structure like a crosslinked structure. This structure serves to raise the glass transition point of the polymer and thereby to improve the heat resistance of the polymer material, leading to improved thermal stability of the record. Besides, this structure is resistant against deformation or molecular movement even at the glass transition temperature or higher temperatures.

Since the polymer material constituting the optical recording medium contains a photoreactive component capable of photoisomerization, irradiation of the optical recording medium with irradiating light or an optical near field results in a difference in the proportion of the isomers between the irradiated area and the non-irradiated area. According to this difference, optical information is recorded as unevenness or differences in optical characteristics, such as a difference in refractive index or absorbance.

The photoreactive component is chemically bonded to the polymer through a covalent bond, an ionic bond, a coordinate bond, etc. If the photoreactive component is merely dispersed in a polymer mechanically, the maximum content of the photoreactive component that could be dispersed uniformly without aggregation is about 20% by weight. To the contrary, the photoreactive component as chemically bonded to the polymer molecule can exist uniformly in a higher proportion, e.g., about 30 to 70% by weight, thus contributing to improvement of response to light in recording.

The following is to describe the 6th aspect of the invention in detail.

[Optical Recording Medium]

The practice of the optical recording medium of the 6th aspect is basically similar to that of the 5th aspect, except for its application to a phase hologram of surface relief type or volume type or to an amplitude hologram.

A phase hologram of surface relief type is an optical recording medium having recorded holographic information as unevenness on the surface of its recording layer by photoisomerization reaction. A phase hologram of volume type is an optical recording medium having recorded holographic information as a change in refractive index in the inside of its recording layer. An amplitude hologram is an optical recording medium having recorded holographic information in its recording layer as a change in amplitude of light caused by a change of transmittance through the recording layer.

The optical recording medium for holography may be a thin film, which can be used alone or together with a substrate. While the thickness of the thin film is not particularly limited, an about 5 $\mu$m or greater thick film is usually used as a volume hologram for ensuring sufficient diffraction efficiency.

Laser light is usually used for recording holographic information on the recording medium for holography. While not limiting, ultraviolet light, visible light and near infrared light are preferred for efficient recording. The same preference applies to the light for reading the recorded holographic information.

Polymer materials constituting the recording layer of the optical recording medium, photoreactive components of the polymer materials, preferred embodiments in the practice, and preferred content of the photoreactive component are the same as those described with respect to the 5th aspect of the invention.

The 6th aspect of the invention offers the following actions and effects.

The optical recording medium according to the 6th aspect can be used as a medium for holography, which is irradiated with object light and reference light to produce an interference fringe to be recorded. More specifically, the property of forming unevenness on the surface of the recording layer can be applied to a phase hologram of surface -relief type; the property of producing a change in refractive index in the recording layer can be applied to a phase hologram of volume type; and the property of making a change in transmittance can be applied to an amplitude hologram.

The optical recording medium for holography of the present invention is advantageous over the conventional holographic recording media comprising inorganic photosensitive materials, such as gelatin dichromate, in that recording can be accomplished in a dry process. In addition to this, the optical recording medium of the invention is advantageous over the conventional holographic recording media comprising photopolymers in that a fixing operation is not necessary.

The thermal stability of the record owing to the characteristics of the polymer material and the improved photoresponse sensitivity owing to the high content of the photoreactive component that have been described with respect to the 5th aspect of the invention also apply to the 6th aspect.

The details of the 7th aspect of the present invention are described below.

[Optical Recording Medium]

The range of the photoreactive component used in the optical recording medium of the 7th aspect is limited as compared with that used in the 5th aspect. That is, the polymer which can be used in the 7th aspect should have chemically bonded thereto a photoreactive component (1) which is capable of reversible photoisomerization and (2) whose molecular orientation can be controlled by light.

In order for a photoreactive component to possess the above characteristics (1) and (2), it is essentially required that the component should have a moiety capable of reversible cis-trans photoisomerization, such as an N=N double bond or a C=C double bond, and that the molecular axes of two trans-forms, with the double bond being taken as fixed, be in different directions. In connection to the latter requirement, an N=N double bond satisfies the requirement whatever molecular structure may be bonded to each side thereof, but a C=C double bond fails to satisfy where it has symmetric molecular structures on its both sides.

With the above exception, the 7th aspect is the same with the 5th aspect in terms of the polymer materials constituting the recording layer of the optical recording medium, the kind of the photoreactive components contained in the polymer materials, preferred embodiments in the practice, and the preferred content of the photoreactive component.

Linearly polarized light can be used for recording information on the optical recording medium. While the recording light is not particularly limited in wavelength, a preferred wavelength is in the vicinity of the maximum absorption wavelength of the dye (photoreactive component) which shows an optical poling effect, at which wavelength the dye exhibits high efficiency in re-orientation on photoisomerization.

Reading of recorded information on the optical recording medium is conducted by using weak linearly polarized light that does not influence the record. The recorded information is detected or read out as a change of transmission based on the optical poling of the recording layer or as a change in reflected light intensity caused by the change in refractive index.

The direction of polarization of reading light is not limited as far as the change in optical characteristics is detected. In principle, a direction perpendicular to the linearly polarized light used for recording shows a greater degree of the change in optical characteristics and is also preferred from the standpoint of sensitivity and S/N ratio.

The wavelength of the reading light is not limited, either. It may be the same or different from that of the recording light. A high sensitivity can generally be secured at wavelengths in the vicinity of the maximum absorption wavelength at which great changes in optical characteristics are detected. Reading light having the same wavelength as that of recording light produces an advantage that the cost as a whole optical system is reduced. Reading is also possible with white light.

Recorded information can be erased by using circularly polarized light, random polarized light or linearly polarized light having a different direction of polarization from that of recording light. When the recording layer is irradiated with such polarized light, the recorded information is erased through the above-mentioned mechanism to restore, as a matter of course, the state that allows re-recording. Similarly to the recording light, it is preferred for efficient erasure that the wavelength of erasing light to be in the vicinity of the maximum absorption wavelength of the dye (photoreactive component).

The 7th aspect has the following actions and effects.

Since the photoisomerization of the photoreactive component is reversible, and the molecular orientation of the photoreactive component can be controlled by light, the optical recording medium is capable of recording, reading out and erasing (to make the recording medium re-writable) information. For example, a photoreactive component (photoresponsive dye) exhibiting large absorption anisotropy and capable of trans-cis photoisomerization undergoes optical poling (molecular orientation control) on being irradiated with linear polarized light. Accordingly, a polymer containing such a photoreactive component can record information with linear polarized light.

The recorded information can be detected or read out as a change in transmitted or reflected light intensity caused by a change in transmission or refractive index when irradiated with, as reading light, weak linearly polarized light that gives no influence on the record.

The recorded information can be erased by irradiation with circularly polarized light or random polarized light to restore the molecular orientation resulting from optical poling to the original random state or by irradiation with relatively intense linearly polarized light having the direction perpendicular to the writing light to change the optical characteristics in the perpendicular direction thereby restoring the optical characteristics in the direction parallel to the polarization to the original state.

Accordingly, information recording, reading out and erasure can be performed with one light source. That is, a recording system can be set up simply by such operations as rotation, attachment or detachment of a polarizing plate, which is advantageous for assembly operation and cost.

The thermal stability of the record owing to the characteristics of the polymer material and the improved photoresponse sensitivity owing to the large content of the photoreactive component that have been described with respect to the 5th aspect of the invention also apply to the 7th aspect.

The 8th aspect of the present invention is then described.

[Optical Recording Medium]

The optical recording medium of the 8th aspect may comprise, in addition to the recording layer comprising a polymer material, other constituent members, such as a substrate, a protective film, and a light reflective film, as in the 5th aspect of the invention.

The optical recording medium is characterized by the contents and mode of the recorded information. The optical recording medium has recorded on its recording layer at least one of pieces of information (1) to (4) previously described. The following finding has made such information recording feasible.

When an informative object (a sample for observation or an object for putting information in) is positioned on the surface of a photosensitive material, and that area of the photosensitive material is irradiated, the photochemical reaction of the photosensitive material which takes place by the optical near field at the part where the informative object is positioned is stronger than the photochemical reaction at other irradiated parts. Based on this finding, the piece of information (1), i.e., an instantaneous form of a moving informative object (e.g., a living object), is recorded by setting a mobile informative object on or above the recording layer of the photosensitive material, irradiating that area of the recording layer, and recording the distribution of the optical near filed generated from the informative object being irradiated as an optical reaction quantity of the photosensitive material. The pieces of information (2) to (4) can be recorded by repeating the above operation two or more times on a moving informative object. The piece of information (4), i.e., a record of change with time of an informative object, includes a record of an informative object which is made to move and to react.

More specifically, a phenomenon that a very small informative object is aligned along the electric field distribution on receiving the radiation pressure of light and then optical near field is recorded. This phenomenon is made use of in optically recording the trace of movement of an informative object while controlling the movement. Where an informative object is accompanied by change in properties or form, the image of the change with time can be obtained. Further, the moving state, cell division or conjugation of a microorganism can be traced.

In carrying out the above-described recording, short pulse light can be used to record a high-speed phenomenon continuously so that the phenomenon may be observed later slowly. Since a single shot for obtaining individual images of continuous recording completes through a single irradiating operation, there is no such a recording failure that may occur where an informative object is a very small moving substance or living organism (especially a microorganism).

While not limiting, the polymer material used in the 5th aspect is particularly preferred for the photosensitive material constituting the recording medium of the 8th aspect. Additionally any known photosensitive polymer materials or non-polymer materials capable of recording an optical near field are employable. The information can be recorded in the similar modes as described for the 5th aspect, for example in the form of unevenness, an change in refractive index, a change in absorbance, or any other known modes of recording. The means for reading the recorded information is arbitrary.

Utilizing an optical near field, the optical recording medium of the 8th aspect can have information recorded at a very high density.

The 8th aspect of the invention produces the following actions and effects.

There is provided an optical recording medium having recorded practically beneficial pieces of information, such as change or movement of an informative object, that could not be achieved by conventional techniques using an optical near field. The optical recording medium has thus acquired an heightened value as a means for furnishing information. Relying on an optical near field, the optical recording medium has recorded information at a high recording density exceeding the limit of light diffraction and thereby having a further heightened value.

The present invention will now be illustrated in greater detail by way of Preparation Examples and Examples, but it should be understood that the present invention is not deemed to be limited thereto. Unless otherwise noted, all the percents are by weight.

Preparation Example
Synthesis of Photoreactive Component

In a mixture of 300 ml of water and 180 ml of a 36% hydrochloric acid aqueous solution was dissolved 30.43 g of 2-methyl-4-nitroaniline, and the solution was cooled to 3° C. To the solution was added a solution of 15.20 g of sodium nitrite in 100 ml of water, and the resulting solution was stirred at 3° C. for 1 hour. A solution of 39.05 g of m-tolyl diethanolamine in a mixture of 300 ml of water and 30 ml of a 36% hydrochloric acid aqueous solution was slowly added thereto over 60 minutes, followed by stirring at 3° C. for 150 minutes to allow the mixture to react.

The reaction mixture was neutralized with 141.6 g of potassium hydroxide dissolved in 700 ml of water, and the crude product was collected by filtration, washed with water, and dried. Recrystallization was repeated three times to give 4-N,N-bis(2-hydroxyethyl)amino-2,2'-dimethyl-4'-nitroazobenzene represented by formula (V) having a melting point of 169° C. in a yield of 62%.

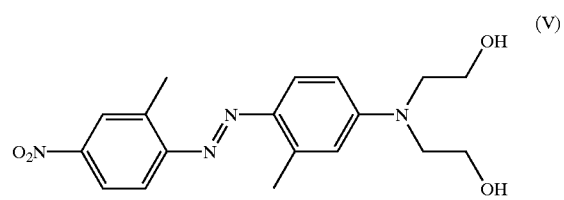

(V)

Preparation of Photoreactive Component-containing Polymer I

In 50 ml of N-methyl-2-pyrrolidone were dissolved 2.000 g of the above prepared 4-N,N-bis(2-hydroxyethyl)amino-2,2'-dimethyl-4'-nitroazobenzene and 2.095 g of 4,4'-diphenylmethane diisocyanate and reacted by stirring at room temperature for 15 minutes and then at 100° C. for 60 minutes. The reaction mixture was cooled to 50° C., and a solution of 0.319 g of trans-2,5-dimethylpiperazine in 20 ml of N-methyl-2-pyrrolidone was added thereto, followed by further reacting for 5 hours while stirring. The reaction mixture was heated to 115° C. under reduced pressure to evaporate 52 ml of N-methyl-2-pyrrolidone slowly over a 150 minute period.

The resulting concentrate was diluted with 180 ml of pyridine and filtered through a 0.1 μm filter. The filtrate was poured into ethanol, and the polymer thus precipitated was collected by filtration. The polymer was further purified by reprecipitation twice to give a polymer represented by formula (VI) (designated polymer I) in a yield of 92%.

Glass transition temperature: 141° C.

Intrinsic viscosity at 30° C. in N-methyl-2-pyrrolidone: 0.69 dl/g

Maximum absorption wavelength: 475 nm

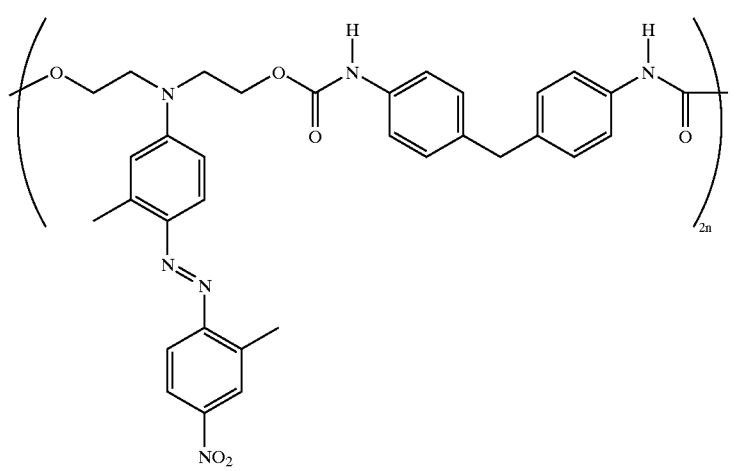

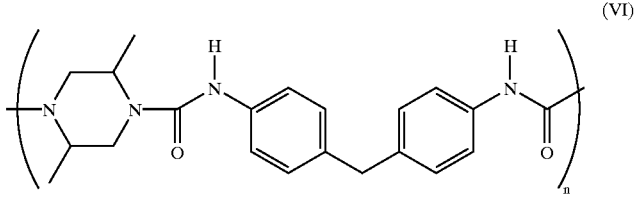

Preparation of Photoreactive Component-containing Polymer II

In a mixture of 5 ml of pyridine and 5 ml of 1,1,2,2-tetrachloroethane were dissolved 0.700 g of the compound of formula (V) and 0.606 g of terephthalic acid chloride, and the mixture was allowed to react at 130° C. for 2 hour while stirring. The reaction mixture was cooled to 30° C., and 0.285 g of 1,3-bis(aminophenoxy)benzene was added thereto to allow the mixture to further react for 3 hours with stirring. The resulting reaction mixture was poured into ethanol, and the precipitate was collected by filtration. The thus obtained polymer was dissolved in N-methyl-2-pyrrolidone, and the solution was poured into water. The precipitate was collected by filtration and dried under reduced pressure to give a polymer represented by formula (VII) (designated polymer II) in a yield of 31%.

Glass transition temperature: 102° C.

Intrinsic viscosity at 30° C. in N-methyl-2-pyrrolidone: 0.18 dl/g

Absorption maximum wavelength: 480 nm

A disk having a hole of 5 mm in diameter was cleaned by ultrasonication and put on the recording medium. A few drops of water having dispersed therein a large number of polystyrene microspheres having a diameter of 500 nm were dropped on the hole of the disk. After allowing the system to stand until water evaporated spontaneously, the area of the recording medium where the polystyrene microspheres were placed (recording area) was irradiated with a laser beam having a beam diameter of about 3 mm and a wavelength of 488 nm emitted from an air-cooled argon laser (output: 20 mW).

Figure 2:
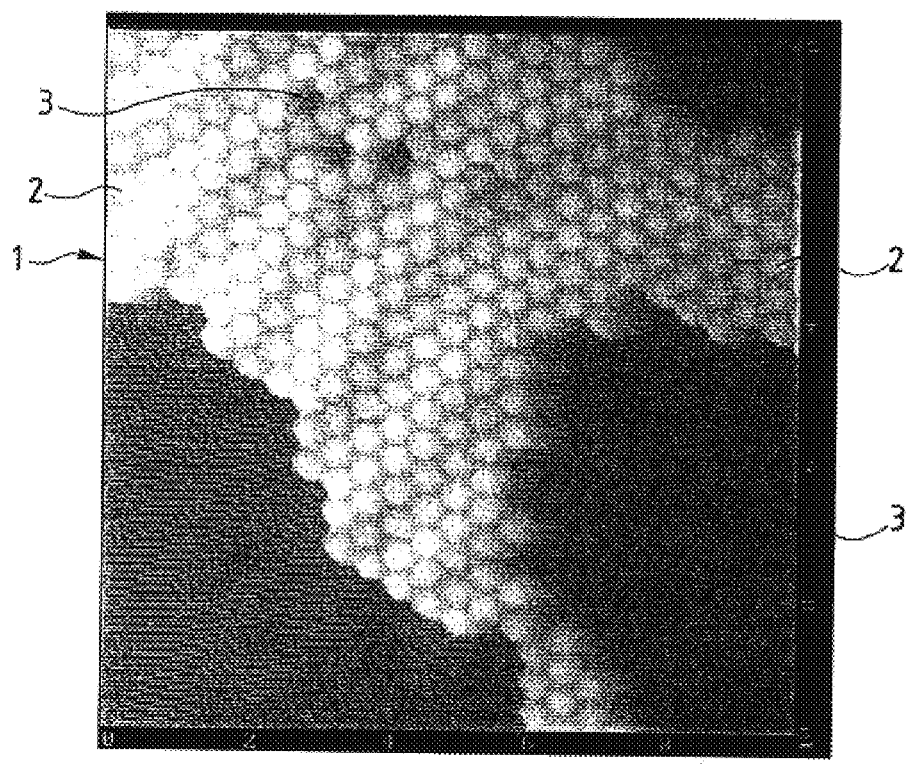

The recording medium was washed with water to remove part of the polystyrene microspheres, and the irradiated area of the recording medium was observed under an atomic force microscope (SPI-3700, manufactured by Seiko Instruments Inc.). The micrographs of the sample taken from different angles are shown in FIGS. 1 and 2. Each micrograph shows microspheres 2 (informative object) remaining on the recording medium 1 and depressions 3 which correspond to the shape of the microspheres having been removed.

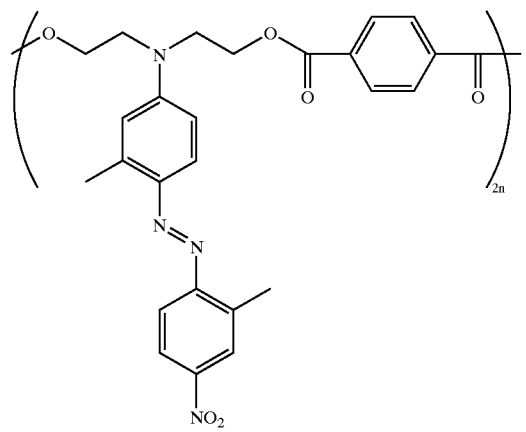

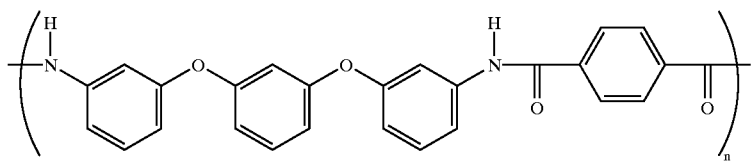

EXAMPLE 1

Preparation of Recording Medium

The polymer I represented by formula (VI) was dissolved in pyridine to prepare a 6.5% by weight polymer solution. After filtration through a 0.2 μm filter, the polymer solution was spin coated on a slide glass at 1000 rpm and dried at 80° C. for 20 hours in vacuo to prepare a thin film as a recording medium. Observation of optical near field distribution in the vicinity of informative object:

EXAMPLE 2

Figure 3:
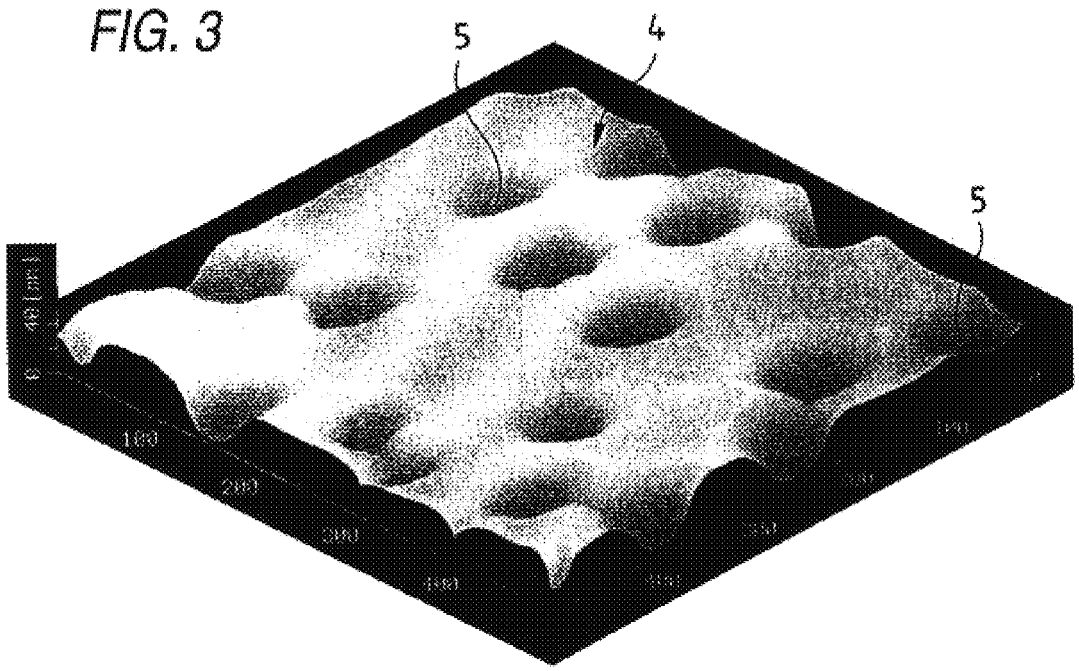
Figure 4:
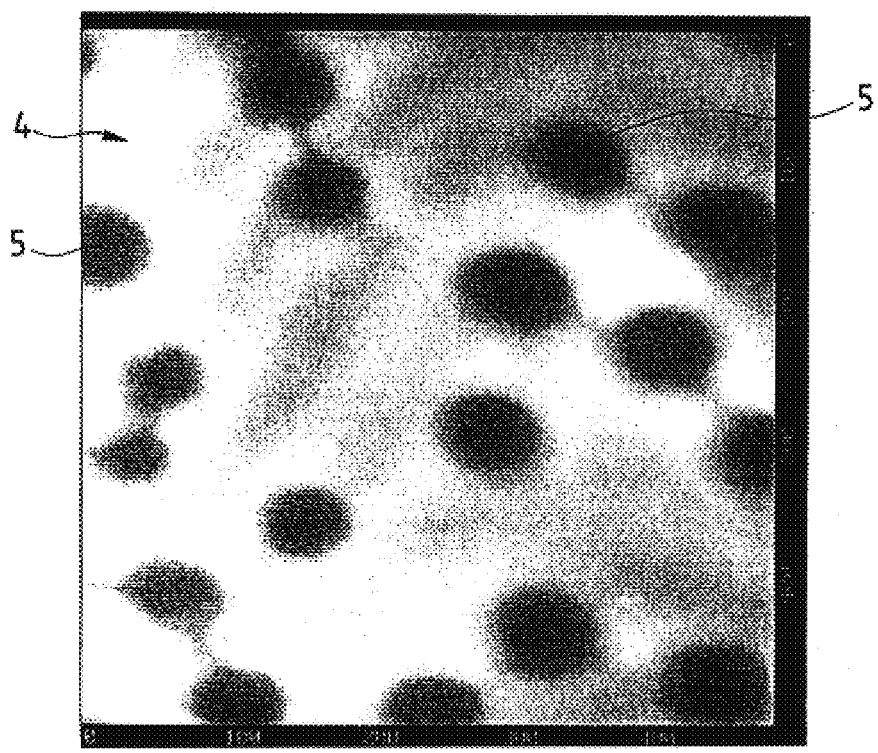

The following experiment was carried out in order to confirm that formation of depressions is by the optical near field generated from an informative object. The same procedure as in Example 1 was repeated, except for using polystyrene microspheres having a diameter of 100 nm, which is about one-fifth of the wavelength of the recording light. The resulting micrographs, taken from different angles, are shown in FIGS. 3 and 4. Each micrograph shows depressions 5 corresponding to the microspheres having been removed from the surface of the recording medium 4.

For reference, the same recording medium was irradiated with no informative object put thereon and observed in the same manner as in Example 1 described above. As a matter of course, no unevenness was observed on the recording medium.

EXAMPLE 3

Preparation of Recording Medium

The polymer I represented by formula (VII) was dissolved in pyridine to prepare a 6.5% polymer solution. After filtration through a 0.2 μm filter, the polymer solution was spin coated on a slide glass at 1000 rpm and dried in vacuo at 80° C. for 20 hours to prepare a thin film having a thickness of about 1 μm as a recording medium.

Bit Data Recording by Depression Forming

The recording medium was irradiated with a condensed beam of an argon laser having a wavelength of 488 nm to record bit data. The bit data were observed through an atomic force microscope (SPI-3700,manufactured by Seiko Instruments Inc.). The condenser used was a ultra-long working distance objective lens manufactured by Mitsutoyo, having an numerical aperture of 0.55 and a magnification of 100. The power of irradiating light was about 200 μW, the beam diameter was about 1 μm, and the exposure time was about 10 msec.

Figure 5:
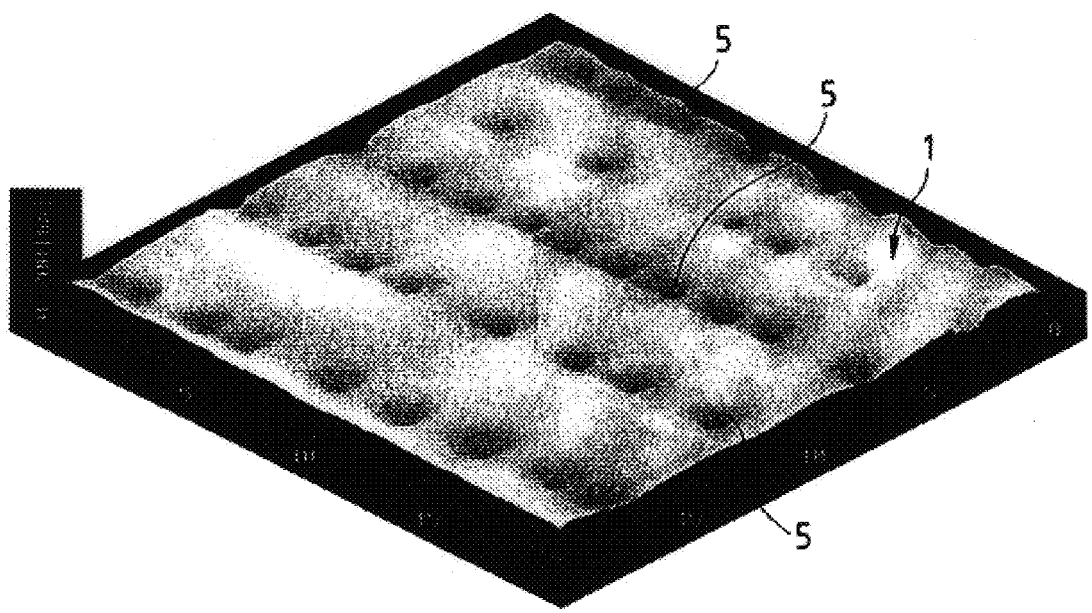
Figure 6:
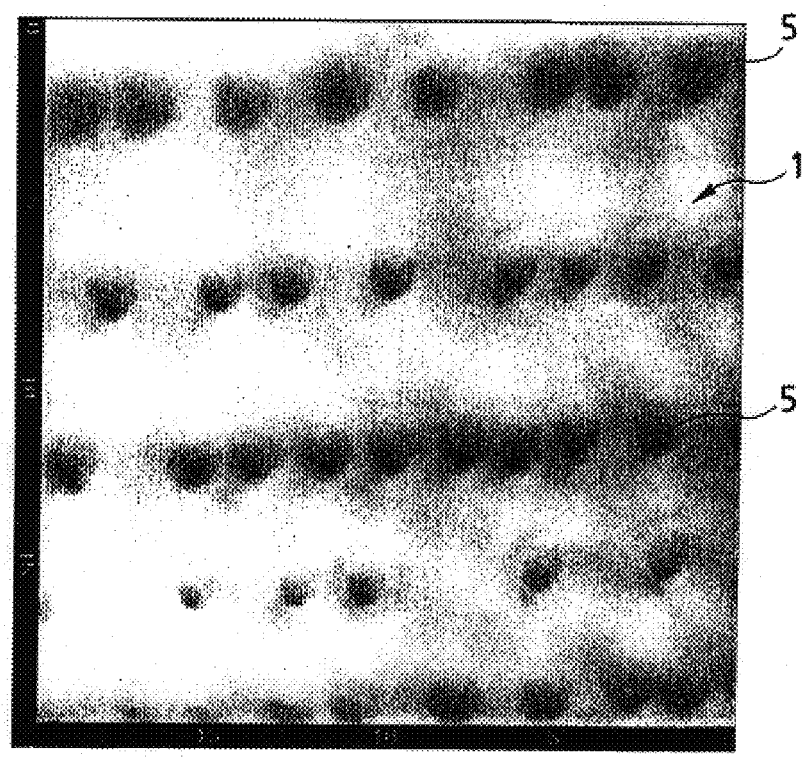

The micrographs of the bit data taken under the atomic force microscope from different angles are shown in FIGS. 5 and 6. Each micrograph shows recorded bit data as depressions 5 at the irradiated spots.

Figure 7:
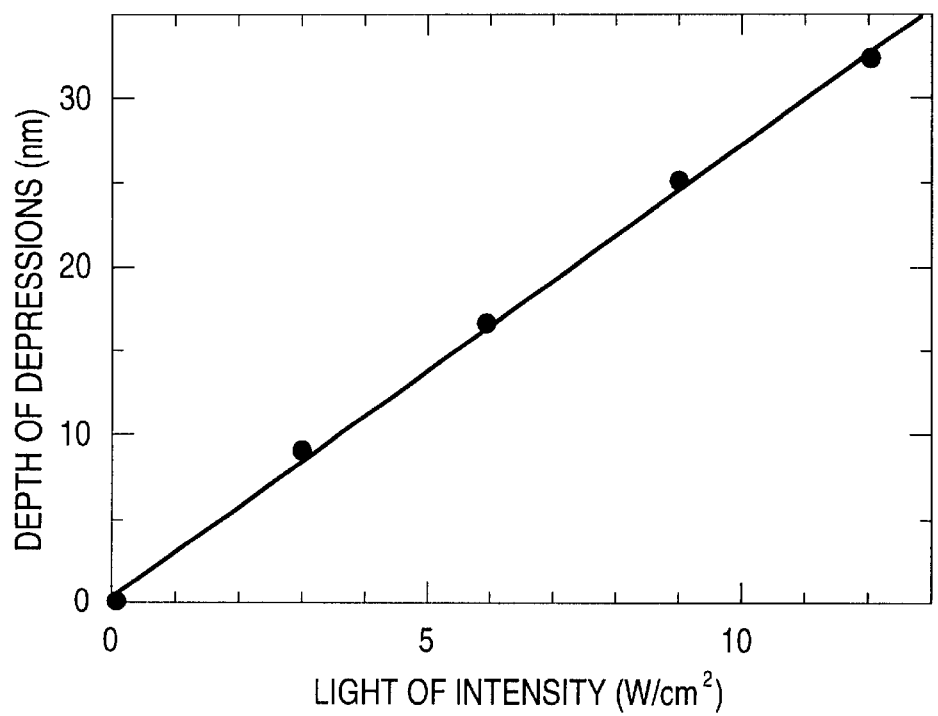
FIG. 7 is a graph of depth of recorded depressions vs. irradiating light intensity.

The recording medium 1 having the bit data was heated at 150° C. for 1 hour and then again observed under the atomic force microscope. No difference by heating was observed in the recorded data, proving excellent heat resistance of the recording film. Relationship between depth of depressions and intensity of irradiating light:

The recording medium was irradiated with an argon laser beam having a wavelength of 488 nm and a varied intensity to form depressions, and the relationship between the light intensity ($W/cm^2$) and the depth of the depressions (nm) was examined. The results obtained are shown in FIG. 7. It is seen from FIG. 7 that the depth of the depressions is proportional to the light intensity of irradiation at least in the measured range of light intensity.

Recording by Change in Absorbance

The recording medium was irradiated with linearly polarized light from an argon laser which had a wavelength of 514.5 nm, an intensity of 1 $W/cm^2$, and whose direction of polarization was in parallel with the recording film for an exposure time of 10 minutes. After the irradiation, the absorbance of the recording film measured at a wavelength of 500 nm showed a decrease by about 22%. When the recording medium was irradiated with laser light having an intensity of 2 $W/cm^2$ for 10 minutes in the same manner, the absorbance at 500 nm showed a decrease by about 58% against the non-irradiated recording medium. In either case, no depression were found formed in the irradiated area unlike the above-described irradiation with argon laser light having a wavelength of 488 nm.

It can be seen from these results that the irradiated area and the non-irradiated area have different absorbances, indicating feasibility of recording information by making use of a difference in absorbance. Such a change in absorbance seems attributable to the photoisomerization of the azobenzene moiety, the photoreactive component of the polymer I, from a trans-form to a cis-form.

Recording by Anisotropy of Absorbance

The recording medium was irradiated with linearly polarized light from an argon laser which had a wavelength of 514.5 nm, an intensity of 1 $W/cm^2$, and whose direction of polarization was in parallel with the recording film for an exposure time of 10 minutes. The polarized light absorption spectrum of the recording medium was measured before and after the irradiation. The spectrum before irradiation was isotropic in the polarization direction parallel with the film, whereas that after irradiation showed anisotropy. That is, in the irradiated recording medium, the absorbance (A2) in the polarization direction perpendicular to the polarization direction of the recording light and parallel with the recording medium was higher than the absorbance (A1) in the polarization direction parallel with the polarization direction of the recording layer.

This results show the difference in anisotropy of absorbance between the irradiated area and the non-irradiated area, proving feasibility of recording information by making use of a difference in anisotropy of absorbance. Such a change in anisotropy of absorbance seems ascribable to the photoisomerization and optical poling effect of the azobenzene moiety, the photoreactive component of polymer I.

Recording by Change in Refractive Index

A recording medium was prepared in the same manner as described above, except that the coating layer was vacuum dried at 100° C. for 20 hours and then at 150° C. for 10 hours. While being heated at 110° C., the recording medium was irradiated with ultraviolet light from a mercury lamp (USH-250BY, manufactured by Ushio Inc.) at an intensity of 0.08 $W/cm^2$ for 4 hours. The UV-irradiated area showed a decrease in refractive index at 830 nm by 0.003.

It is seen that the UV-irradiated area and non-irradiated area show different refractive indices, which can be used for recording information. When the recording medium having recorded the change in refractive index in this manner was heated at 110° C. for 30 minutes, the refractive index was unchanged, proving the recording medium to be excellent in thermal stability. Recording by change in anisotropy of refractive index:

A recording medium was prepared in the same manner as described above, except that the coating layer was vacuum dried at 100° C. for 20 hours. The resulting recording medium was heated at 110° C. for 4 hours, and the heat-induced change in anisotropy of refractive index was measured. Taking the refractive index for light having a wavelength of 830 nm and a polarization direction parallel to the recording layer as n1, while that for light having the same wavelength and a polarization direction perpendicular to the recording layer being taken as n2, the refractive index anisotropy, defined as n1–n2, was 0.022 before heating. On heating, it decreased to 0.016.

Heating a material locally by irradiation is sufficiently possible with known techniques. The techniques can be applied to produce a difference in refractive index anisotropy between an irradiated area and a non-irradiated area, thereby making it feasible to record information as a difference in refractive index anisotropy.

EXAMPLE 4

Holography

Figure 8:
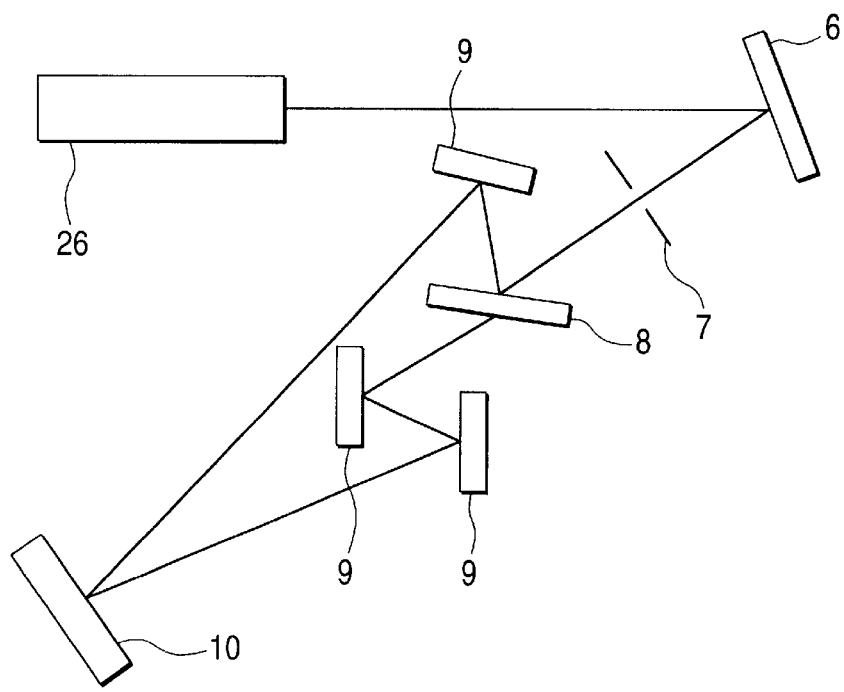
FIG. 8 shows the optical system used in Examples.

Interference of light was recorded on the recording medium prepared in Example 3 by using a two beam interference aligner shown in FIG. 8. In FIG. 8, a beam having a wavelength of 488 nm emitted from an argon laser light source 26 was reflected on a mirror 6 and passed through a pin hole 7 (diameter: 2 nm) for eliminating spatial noise of the laser beam to obtain a uniform interference pattern. The beam was then split into two beams by a beam splitter 8. The optical path and intensity ratios of the beams were made equal by means of a plurality of mirrors 9 arranged in proper positions, and the two beams entered a recording medium 10. The grating space was adjusted according to the angle of incidence. The exposure was continued for 10 minutes.

Figure 9:
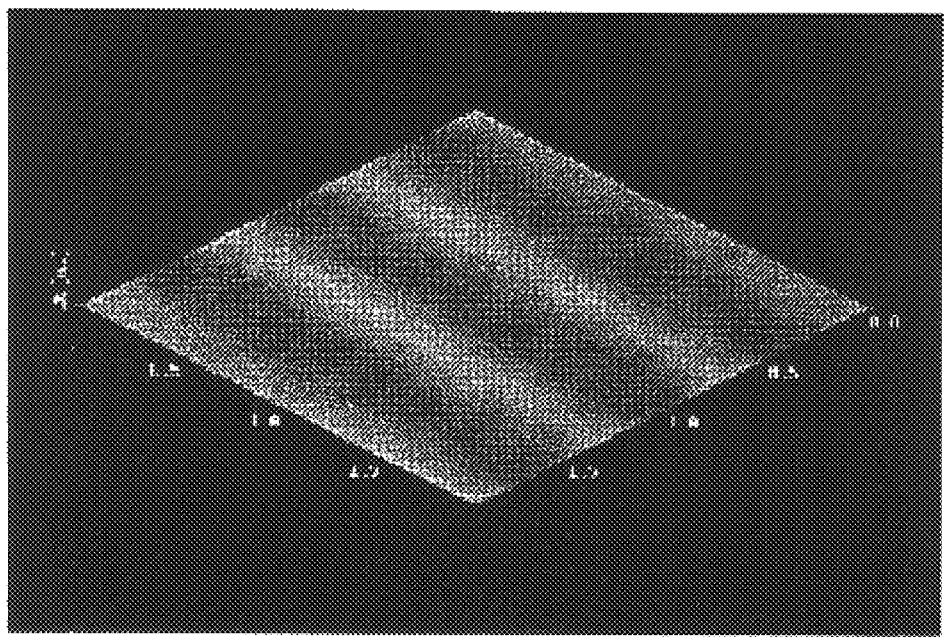
FIG. 9 is a micrograph obtained under an atomic force microscope in Example.
Figure 10:
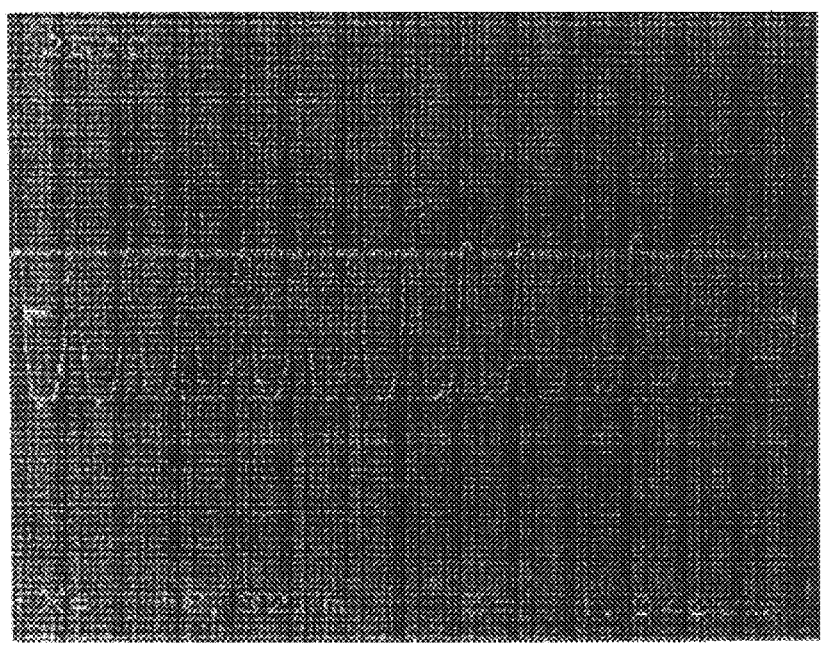
FIG. 10 shows the results of measuring the shape of a grating in Example.

The surface profile of the irradiated recording medium 10 was observed through an atomic force microscope. As shown in the micrograph of FIG. 9, a recorded interference pattern of sine waves was observed. Examination on the relationship between irradiation energy and depth of depressions based on the results of observation revealed that the depth of depressions are proportional to the irradiation energy. This means that the intensity of interference light can be recorded as such on the recording medium 10. The recording medium 10 was thus proved to have excellent performance as a hologram. When the irradiated recording medium 10 was heat treated at 130° C. for 1 hour, no change in image was observed, proving excellent heat stability.

Applicability as Grating Coupler

Figure 12:
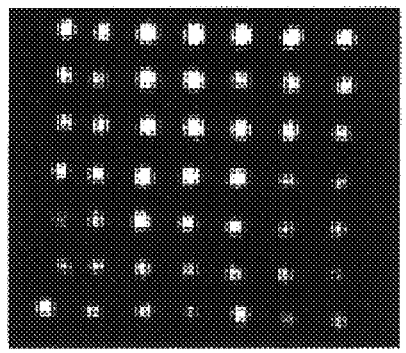
FIGS. 12A, 12B, and 12C show the state of recording, erasure, and re-recording of information, respectively.
Figure 12:
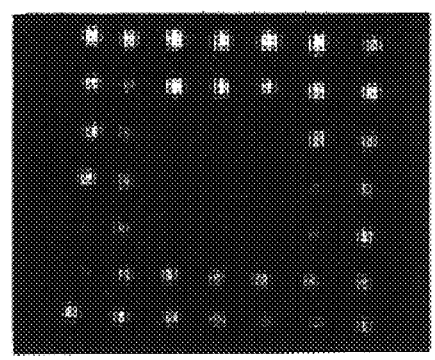
Figure 12:
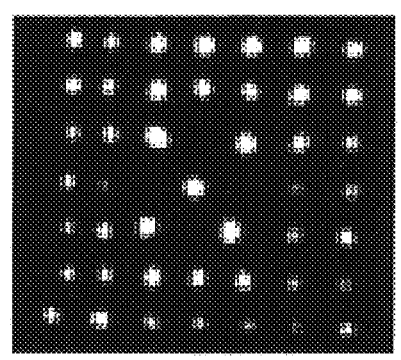

An interference pattern of third harmonic waves of an Nd:YAG laser (wavelength: 355 nm) was recorded on the recording medium using the two beam interference aligner shown in FIG. 8. The results obtained are shown in FIG. 12, in which a neat sine wave pattern having a frequency of 8 $\mu$m is recorded, proving that the recording medium has excellent performance as a hologram. The grating pattern prepared is applicable as a grating coupler of a waveguide, etc. Experiments on optical input characteristics revealed an input efficiency of 10% or higher.

EXAMPLE 5

Recording, Reading Out, Erasure and Re-recording of Information

Figure 11:
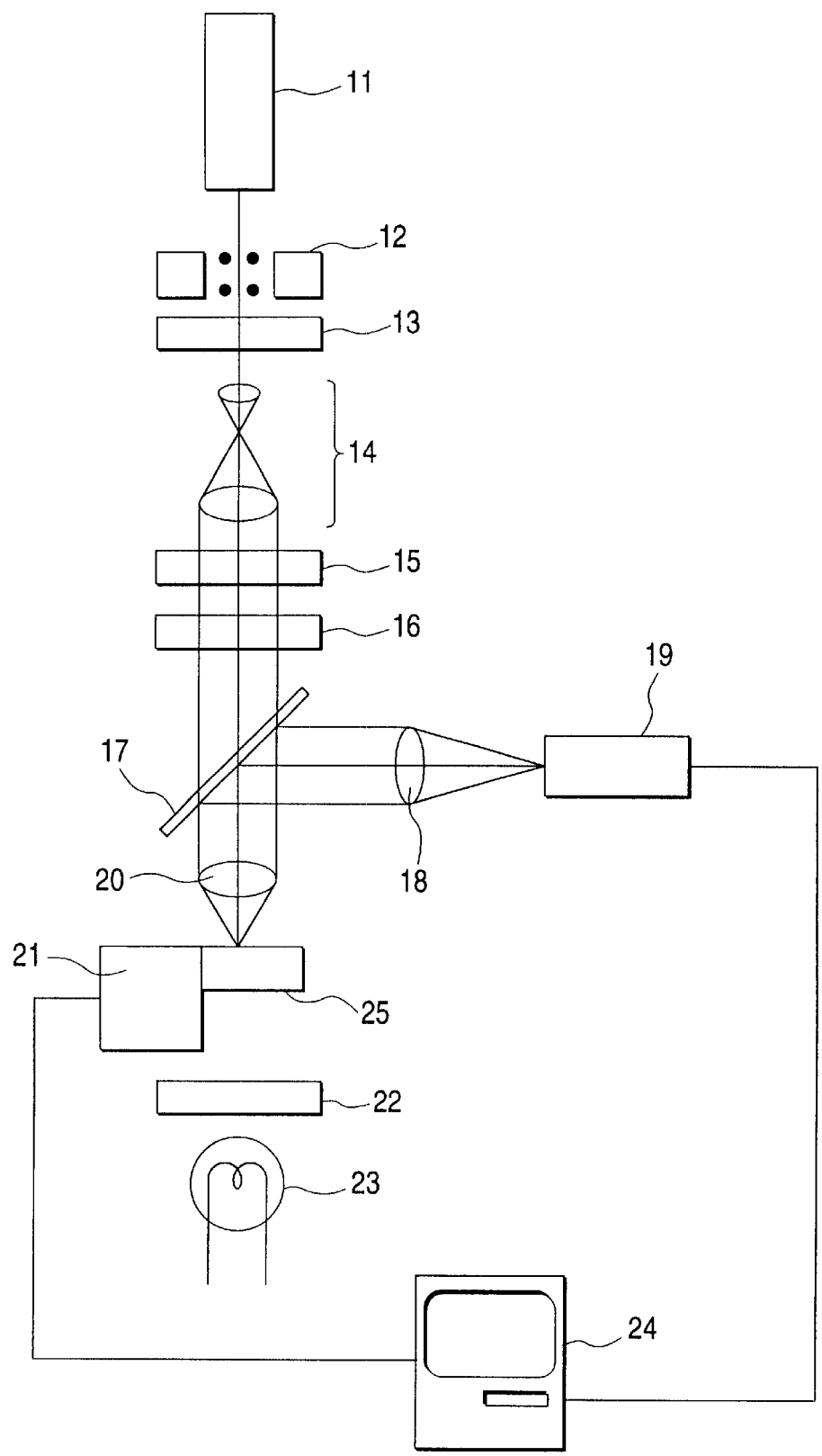
FIG. 11 shows another optical system used in Example.

Information was recorded, read out, erased, and re-recorded on the optical recording medium prepared in Example 3 by use of an optical system shown in FIG. 11. The optical system of FIG. 11 is composed of an argon laser light source 11, a shutter 12, an ND filter 13, a beam expander 14, a quarter-wave plate 15, Glan-Thomson prisms 16 and 22, a beam splitter 17, a lens 18, a charge coupled device (CCD) 19, an objective lens 20, an X-Y-Z stage 21, a white light source 23, and a computer 24.

A recording medium 25 was set on the X-Y-Z stage as shown and irradiated with laser light having a wavelength of 514.5 nm emitted from the argon laser light source 11 for ⅟32 second per spot, the laser light having been linearly polarized and condensed by the objective lens 20 to a beam diameter of about 1 $\mu$m. Recording was carried out on the entire surface of the recording medium 25 while changing the position with the X-Y-Z stage. After the recording completed, the recording medium 25 was illuminated from its back side with white light from the light source 23, and the transmitted light was detected by the CCD 19. The image obtained is shown in FIG. 12A. The white spots are the recorded area. It was thus confirmed that information can be recorded and reproduced satisfactorily.

Then the direction of polarization of the linear polarized light used above for recording was rotated at 90°. Central nine spots out of the white spots of FIG. 12A were irradiated with the polarized light, and the record was detected again in the same manner as described above. The resulting image is shown in FIG. 12B. The central nine spots had been erased, lending confirmation to satisfactory erasure of information.

The recording medium having information recorded and having part of the recorded information erased was again subjected to recording. Five spots were recorded on the area from which nine spots had been erased in the same manner as described above. The reproduced image of the recording medium is shown in FIG. 12C. Satisfactory re-recording on the once erased area of the recording medium was thus confirmed.

While the invention has been described in detail and with reference to specific examples thereof, it will be apparent to one skilled in the art that various changes and modifications can be made therein without departing from the spirit and scope thereof.

What is claimed is:

1. An optical recording method, comprising:
   constituting a recording layer of a photosensitive material capable of undergoing a storable and detectable photochemical reaction;
   setting a three-dimensional informative object on or above the recording layer at such a position that an optical near field generated from the informative object may reach the recording layer;
   irradiating without the use of a mask at least the area of the recording layer where the informative object is positioned with light to cause the informative object to generate the optical near field; and
   recording the distribution of the optical near field on the photosensitive material as a photoreacting quantity of the photosensitive material.

2. The optical recording method according to claim 1, wherein said informative object is made of a material which transmits light for irradiation.

3. The optical recording method according to claim 1, wherein said informative object has a size of 100 nm or smaller.

4. The optical recording method according to claim 1, wherein said light for irradiation is laser light.

5. The optical recording method according to claim 1, wherein said photosensitive material is at least one of a material capable of forming unevenness in accordance with its photoreacting quantity to record the distribution of the optical near field, a material capable of changing its refractive index in accordance with its photoreacting quantity to record the distribution of the optical near field, a material capable of changing its light absorbance in accordance with its photoreacting quantity to record the distribution of the optical near field, a material capable of developing a potential difference in accordance with its photoreacting quantity to record the distribution of the optical near field, and a material containing a photoreactive component capable of changing its degree of orientation in accordance with its photoreacting quantity to record the distribution of the optical near field.

6. The optical recording method according to claim 5, wherein said photosensitive material is a photoreacting polymer material capable of forming unevenness in accordance with its photoreacting quantity to record the distribution of the optical near field.

7. The optical recording method according to claim 5, wherein said photosensitive material is a photorefractive material capable of changing its refractive index in accordance with its photoreacting quantity to record the distribution of the optical near field.

8. The optical recording method according to claim 1, wherein said irradiating is conducted in a state that the informative object is set at a position within a 100 nanometers' distance from the recording layer.

9. The optical recording method according to claim 1, wherein said irradiating is conducted in a state that the informative object is set in contact with the recording layer.

10. The optical recording method according to claim 1, which further comprises observing the recorded distribution of the optical near field by an observing means selected in conformity with the mode of recording.

11. The optical recording method according to claim 10, wherein said photosensitive material is at least one of a material capable of forming unevenness in accordance with its photoreacting quantity to record a distribution of the optical near field, a material capable of changing its refractive index in accordance with its photoreacting quantity to record the distribution of the optical near field, a material capable of changing its light absorbance in accordance with its photoreacting quantity to record the distribution of the optical near field, a material capable of developing a potential difference in accordance with its photoreacting quantity to record the distribution of the optical near field, and a material containing a photoreactive component capable of changing its degree of orientation to record the distribution of the optical near field.

12. The optical recording method according to claim 11, wherein said photosensitive material is a photoreactive polymer material capable of forming unevenness in accordance with its photoreacting quantity to record the distribution of the optical near field.

13. The optical recording method according to claim 11, wherein said photosensitive material is a photorefractive material capable of changing its refractive index in accordance with its photoreacting quantity to record the distribution of the optical near field.

14. The optical recording method according to claim 10, wherein said distribution of the optical near field is recorded as a change in refractive index or absorbance of the photosensitive material, and said observing is carried out with a scanning optical near field microscope.

15. The optical recording method according to claim 10, wherein said distribution of the optical near field is recorded as generation of a potential difference on the photosensitive material, and said observing is carried out with a surface potential microscope.

16. The optical recording method according to claim 1, wherein said setting is conducted in a state that the informative object is set on the recording layer.

17. An optical recording method, comprising:
constituting a recording layer of a photosensitive material capable of undergoing a storable and detectable photochemical reaction;
setting an informative object on or above the recording layer at such a position that an optical near field generated from the informative object may reach the recording layer;
irradiating at least the area of the recording layer where the informative object is positioned with light to cause the informative object to generate the optical near field; and
recording the distribution of the optical near field on the photosensitive material as a photoreacting quantity of the photosensitive material, wherein said informative object has a size of 25 nm or smaller.

18. An optical recording method, comprising:
constituting a recording layer of a photosensitive material capable of undergoing a storable and detectable photochemical reaction;
setting an informative object on or above the recording layer at such a position that an optical near field generated from the informative object may reach the recording layer;
irradiating at least the area of the recording layer where the informative object is positioned with light to cause the informative object to generate the optical near field; and
recording the distribution of the optical near field on the photosensitive material as a photoreacting quantity of the photosensitive material,
wherein said photosensitive material is a photoconductive material capable of developing a potential difference in accordance with its photoreacting quantity to record the distribution of the optical near-field.

19. An optical recording method, comprising:
constituting a recording layer of a photosensitive material capable of undergoing a storable and detectable photochemical reaction;
setting an informative object on or above the recording layer at such a position that an optical near field generated from the informative object may reach the recording layer;
irradiating at least the area of the recording layer where the informative object is positioned with light to cause the informative object to generate the optical near field; and
recording the distribution of the optical near field on the photosensitive material as a photoreacting quantity of the photosensitive material, wherein said irradiating and recording are repeated two or more times in accordance with the movement of the informative object.

20. An optical recording method, comprising:
constituting a recording layer of a photosensitive material capable of undergoing a storable and detectable photochemical reaction;
setting an informative object on or above the recording layer at such a position that an optical near field generated from the informative object may reach the recording layer;
irradiating at least the area of the recording layer where the informative object is positioned with light to cause the informative object to generate the optical near field; and
recording the distribution of the optical near field on the photosensitive material as a photoreacting quantity of the photosensitive material, which further comprises observing the recorded distribution of the optical near field by an observing means selected in conformity with the mode of recording, wherein said photosensitive material is a photoconductive material capable of developing a potential difference in accordance with its photoreacting quantity to record the distribution of the optical near-field.

21. An optical recording method, comprising:
constituting a recording layer of a photosensitive material capable of undergoing a storable and detectable photochemical reaction;
setting an informative object on or above the recording layer at such a position that an optical near field generated from the informative object may reach the recording layer;
irradiating at least the area of the recording layer where the informative object is positioned with light to cause the informative object to generate the optical near field; and
recording the distribution of the optical near field on the photosensitive material as a photoreacting quantity of the photosensitive material, which further comprises observing the recorded distribution of the optical near field by an observing means selected in conformity with the mode of recording, wherein said irradiating is repeated at a given interval with pulse light to record a changing history of the informative object.

22. An optical recording system comprising:

a recording layer on or above which a three-dimensional informative object is positioned in the absence of a mask and which is constituted by a photosensitive material capable of undergoing a storable and detectable photochemical reaction; and a light source capable of irradating for a time at least the area of the recording layer where the informative object is positioned.

23. The optical recording system according to claim 22, wherein the informative object is positioned on the recording layer.

* * * * *